(12) United States Patent
Porta et al.

(10) Patent No.: US 6,265,351 B1
(45) Date of Patent: Jul. 24, 2001

(54) PHENYLPYRAZOLES WITH A HERBICIDAL ACTIVITY

(75) Inventors: Piero La Porta; Franco Bettarini, both of Novara; Giovanni Meazza, Saronno; Gregorio Valea, Novara; Ernesto Signorini, Malnate; Domenico Portoso, Lodi, all of (IT)

(73) Assignee: Isagro Ricerca S.r.L., Milan (IT)

( * ) Notice: Subject to any disclaimer, the term of this patent is extended or adjusted under 35 U.S.C. 154(b) by 0 days.

(21) Appl. No.: 09/631,827

(22) Filed: Aug. 3, 2000

(30) Foreign Application Priority Data

Aug. 5, 1999 (IT) ................................. MI99A1766

(51) Int. Cl.$^7$ .................................... A01N 43/82
(52) U.S. Cl. .................. 504/263; 548/142; 548/186; 548/187; 548/205; 548/248; 548/365.1; 548/365.7
(58) Field of Search ............... 548/142, 365.1, 548/365.7; 504/263

(56) References Cited

U.S. PATENT DOCUMENTS 5,064,850 * 11/1991 Audia ................. 548/365.7
6,121,201   9/2000 Pulman et al. .

FOREIGN PATENT DOCUMENTS

| 196 22 189 A1 | 12/1997 | (DE) . |
| WP 98/41093 | 9/1998 | (WO) . |
| WO 99/38861 | 8/1999 | (WO) . |

* cited by examiner

*Primary Examiner*—Robert W. Ramsuer
(74) *Attorney, Agent, or Firm*—Oblon, Spivak, McLelland, Maier & Neustadt, P.C.

(57) ABSTRACT

The invention relates to phenylpyrazoles having general formula (I):

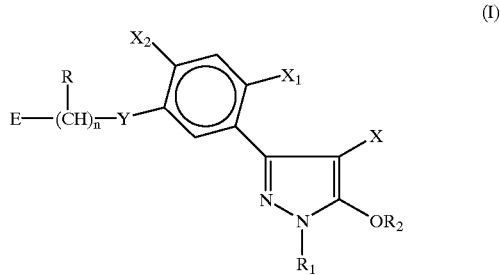

The compounds having formula (I) have a high herbicidal activity and are used for controlling weeds in the agronomic field.

9 Claims, No Drawings

PHENYLPYRAZOLES WITH A HERBICIDAL ACTIVITY

The present invention relates to new phenylpyrazoles. More specifically, the present invention relates to new phenylpyrazoles having a high herbicidal activity, the processes for their preparation and their use as herbicides for controlling weeds in agricultural crops.

Phenylpyrazoles with a herbicidal activity are described, among others, in European patent applications EP 361,114, EP 447,055, EP 839,808 and Japanese patent applications JP 3,151,367, JP 3,163,063.

These products, however, are not always satisfactory from the point of view of herbicidal activity with respect to weeds, and in addition have a poor selectivity, with the result that they are generally phytotoxic also with respect to the most important agricultural crops.

The Applicant has now found new phenylpyrazoles which not only have a high herbicidal activity with respect to numerous weeds but, at the same time, also have a low phytotoxicity towards various crops of agrarian interest and can therefore be used as selective herbicides.

The object of the present invention therefore relates to new phenylpyrazoles having general formula (I):

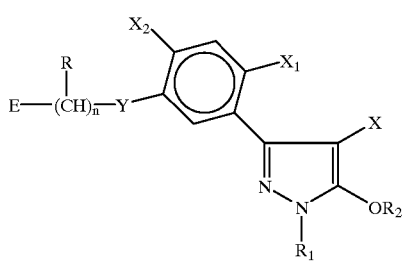

(I)

wherein:
$R_1$ and $R_2$, the same or different, represent a $C_1$–$C_4$ alkyl or haloalkyl group;
X represents a halogen atom;
$X_1$ represents a hydrogen atom, a chlorine atom or a fluorine atom;
$X_2$ represents a chlorine atom, a bromine atom, a $C_1$–$C_4$ haloalkyl group, a $C_1$–$C_4$ haloalkoxyl group;
Y represents an oxygen atom or a sulfur atom;
R represents a hydrogen atom or a $C_1$–$C_4$ alkyl group;
n represents 0 or 1;
E represents one of the following heterocyclic groups:
2-furanyl, 3-furanyl, 2-thiophenyl, 3-thiophenyl, 2-pyrrolyl, 3-pyrrolyl, 2-imidazolyl, 4-imidazolyl, 5-imidazolyl, 3-pyrazolyl, 4-pyrazolyl, 5-pyrazolyl, 1,2,4-triazol-3-yl, 1,2,4-triazol-5-yl, 1,2,4-triazol-3-on-5-yl, 1,2,3-triazol-4-yl, 1,2,3-triazol-5-yl, 5-tetrazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-oxadiazol-2-yl, 1,3,4-oxadiazol-2-on-5-yl, 1,3,4-thiadiazol-2-yl, 1,3,4-thiadiazol-2-on-5-yl, 1,2,4-oxadiazol-3-yl, 1,2,4-oxadiazol-5-yl, 1,2,4-thiadiazol-3-yl, 1,2,4-thiadiazol-5-yl; said groups can be substituted by one or more groups—the same or different—selected from a halogen atom, a $C_1$–$C_6$ alkyl or haloalkyl group, a $C_1$–$C_6$ alkoxyl or haloalkoxyl group, a $C_2$–$C_6$ alkoxyalkyl or haloalkoxyalkyl group, a $C_1$–$C_6$ alkylthio or haloalkylthio group, a $C_1$–$C_6$ alkylsulfinic or haloalkylsulfinic group, a $C_1$–$C_6$ alkylsulfonic or haloalkylsulfonic group, an alkoxycarbonyl or haloalkoxycarbonyl group, an aminocarbonyl group optionally substituted by one or two $C_1$–$C_4$ alkyl groups or by a $C_2$–$C_5$ alkylene chain, a cyano group, a formyl group, an alkylcarbonyl or haloalkylcarbonyl group, an alkoxyiminoalkyl or haloalkoxyiminoalkyl group, a phenyl group optionally substituted, in turn, by halogen atoms, $C_1$–$C_4$ alkyl or haloalkyl groups, $C_1$–$C_4$ alkoxyl or haloalkoxyl groups.

Specific examples of compounds having general formula (I) which are of interest for their herbicidal activity are:
1) 4-chloro-3-[4-chloro-2-fluoro-5-(5-trifluoromethyl-1,3,4-thiadiazol-2-yloxy)phenyl]-5-fluoromethoxy-1-methylpyrazole;
2) ethyl 2-[2-chloro-5-(4-chloro-5-difluoromethoxy-1-methylpyrazol-3-yl)-4-fluoro-phenoxymethyl]-3-furancarboxylate;
3) 4-chloro-3-[4-chloro-2-fluoro-5-(5-methyl-1,3,4-thiadiazol-2-yloxy)phenyl]-5-difluoromethoxy-1-methylpyrazole;
4) 4-chloro-3-[4-chloro-2-fluoro-5-(5-ethylthio-1,3,4-thiadiazol-2-yloxy)phenyl]-5-difluoromethoxy-1-methylpyrazole;
5) 4-chloro-3-[4-chloro-2-fluoro-5-(5-ethylsulfonyl-1,3,-4-thiadiazol-2-yloxy)phenyl]-5-difluoromethoxy-1-methylpyrazole;
6) 4-chloro-3-{4-chloro-2-fluoro-5-[5-(1,1,2,2-tetrafluoroethylthio)-1,3,4-thiadiazol-2-yloxy]phenyl}-5-difluoromethoxy-1-methylpyrazole;
7) 4-chloro-3-[4-chloro-2-fluoro-5-(5-trifluoromethyl-1,3,4-thiadiazol-2-yloxy)phenyl]-5-(1,1,2,2-tetrafluoroethoxy)-1-methylpyrazole;
8) ethyl 2-{2-chloro-5-[4-chloro-5-(1,1,2,2-tetrafluoroethoxy)-1-methylpyrazol-3-yl]-4-fluorophenoxymethyl}-3-furancarboxylate;
9) methyl 3-[2-chloro-5-(4-chloro-5-difluoromethoxy-1-methylpyrazol-3-yl)-4-fluoro-phenoxymethyl]-2-thiophenecarboxylate;
10) 4-chloro-3-[4-chloro-2-fluoro-5-(5-formylthiophen-2-yloxy)phenyl]-5-difluoromethoxy-1-methylpyrazole;
11) 4-chloro-3-[4-chloro-2-fluoro-5-(5-methoxyiminomethylthiophen-2-yloxy)phenyl]-5-difluoromethoxy-1-methylpyrazole;
12) 4-chloro-3-[4-chloro-2-fluoro-5-(4-formyl-2-methylthiazol-5-yloxy)phenyl]-5-difluoromethoxy-1-methylpyrazole;
13) 4-chloro-3-[4-chloro-2-fluoro-5-(4-ethoxyiminomethyl-2-methylthiazol-5-yloxy)phenyl]-5-difluoromethoxy-1-methyl-pyrazole;
14) 4-chloro-3-[4-chloro-2-fluoro-5-(2-methylthiazol-4-yl)methoxyphenyl]-5-difluoromethoxy-1-methyl-pyrazole;
15) 4-chloro-3-[4-chloro-2-fluoro-5-(5-bromo-2-methylthiazol-4-yl)methoxyphenyl] -5-difluoromethoxy-1-methylpyrazole;
16) 4-chloro-3-[4-chloro-2-fluoro-5-(4-formyl-1,3-dimethylpyrazol-5-yloxy)phenyl]-5-difluoromethoxy-1-methylpyrazole.
17) 4-chloro-3-[4-chloro-5-(1,3-dimethyl-4-methoxyimino-methylpyrazol-5-yloxy)-2-fluorophenyl]-5-difluoromethoxy-1-methylpyrazole
18) ethyl 5-[2-chloro-5-(4-chloro-5-difluoromethoxy-1-methylpyrazol-3-yl)-4-fluorophenoxymethyl-3-isoxazole-carboxylate;
19) ethyl 5-[2-chloro-5-(4-chloro-5-difluoromethoxy-1-methylpyrazol-3-yl)-4-fluorophenoxymethyl-3-furoate;
20) ethyl 2-[2-chloro-5-(4-chloro-5-difluoromethoxy-1-methylpyrazol-3-yl)-4-fluorophenoxymethyl-4-thiaz-ole-carboxylate;

21) 4-chloro-3-[4-chloro-5-(5-ethyl-1,3,4-thiadiazol-2-yloxy)-2-flurophenyl]-5-difluoromethoxy-1-methylpyrazole;
22) 4-chloro-3-(4-chloro-2-fluoro-5-(5-isopropyl-1,3,4-thiadiazol-2-yloxy)phenyl]-5-difluoromethoxy-1-methylpyrazole;
23) 4-chloro-3-[4-chloro-2-fluoro-5-(5-methoxymethyl-1,3,4-thiadiazol-2-yloxy)phenyl]-5-difluoromethoxy-1-methylpyrazole;
24) 4-chloro-3-{4-chloro-2-fluoro-5-[5-(3-trifluoromethyl-phenyl)-1,3,4-thiadiazol-2-yloxy]phenyl}-5-difluoromethoxy-1-methylpyrazole;
25) 4-chloro-3-[4-chloro-2-fluoro-5-(1-methyl-2-trifluoromethyl-1,3,4-thiadiazol-5-yloxy)phenyl]-5-difluoromethoxy-1-methylpyrazole;
26) 4-chloro-3-[4-chloro-2-fluoro-5-(3-nitrothien-2-yloxy)phenyl]-5-difluoromethoxy-1-methylpyrazole A further object of the present invention relates to processes for the preparation of compounds having general formula (I).

The compounds having general formula (I) can be obtained starting from a phenyl-pyrazolone having general formula (II) by reaction with a compound having general formula (III) to give a phenylpyrazolyl ether having general formula (IV) which is subsequently converted to the end product having general formula (I) by treatment with a halogenating agent, according to reaction scheme A.

Alternatively, the compounds having general formula (I) can be obtained from a phenylpyrazole having general formula (V) by treatment with a compound having general formula (VI), according to reaction scheme B.

The reaction between the compound having general formula (II) and the compound having general formula (III) is preferably carried out in the presence of one or more inert organic solvents and in the presence of an inorganic or organic base, at a temperature ranging from −10° C. to the boiling point of the reaction mixture.

Organic solvents which can be used for the purpose are for example aromatic hydrocarbons (benzene, toluene, xylene, chlorobenzene, etc.), ethers (diethyl ether, diisopropyl ether, dimethoxyethane, dioxane, tetrahydrofuran, etc.), esters (ethyl acetate, etc.), alcohols and glycols (methanol, ethanol, methylcellosolve, ethylene glycol, etc.), ketones (acetone, methylethylketone, methylpropylketone, methylisobutylketone, etc.), nitrites (acetonitrile, benzonitrile, etc.), aprotic dipolar solvents (dimethylformamide, dimethylacetamide, hexamethylphosphorotriamide, dimethyl-sulfoxide, sulfolane, N-methylpyrrolidone, etc.).

Inorganic bases which can be used for the purpose are, for example, sodium or potassium hydrides, hydroxides and carbonates.

Organic bases which can be used for the purpose are, for example, triethylamine, pyridine, 4-dimethylamino-pyridine, diazabicyclo-octane (DABCO), diazabicycloundecene (DBU).

The reaction can also be advantageously carried out in a biphasic system using, as solvents, water and an organic solvent immiscible therewith, in the presence of phase transfer catalysts, according to the procedure described by Dehmlow and Dehmlow in "Phase Transfer Catalysis" (1983), Verlag Chemie.

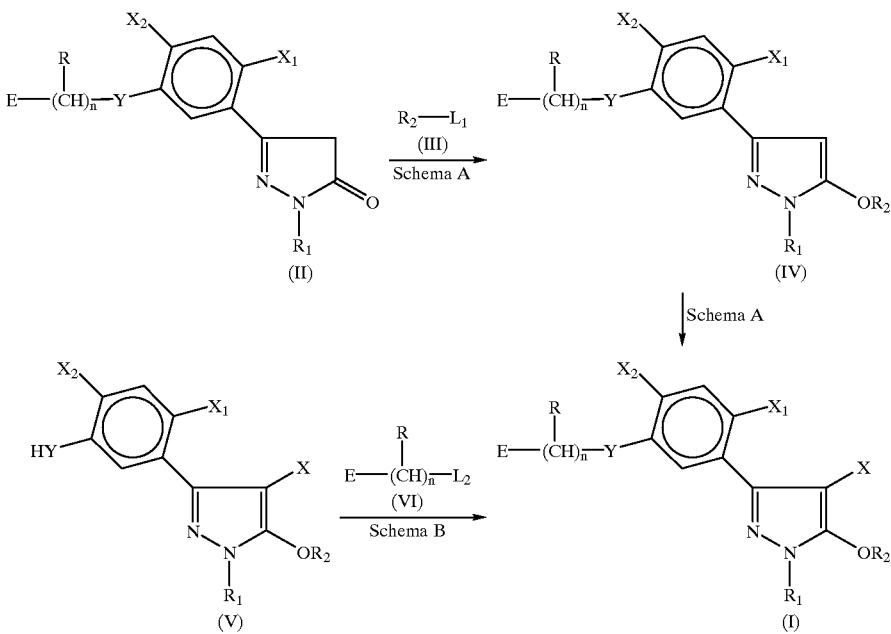

In these formulae, E, R, $R_1$, $R_2$, X, $X_1$, $X_2$, Y and n have the same meanings described above;
$L_1$ represents a halogen atom or an $OSO_2R_L$ group wherein $R_L$ represents a $C_1$–$C_4$ alkyl or haloalkyl group or a phenyl optionally substituted by $C_1$–$C_4$ alkyl or haloalkyl groups;
$L_2$ represents an $L_1$ group or, when n=0, it may also represent an $SO_2R_L$ group wherein $R_L$ has the meanings defined above.

The halogenation reaction of the product having general formula (IV) can be carried out in an inert organic solvent, at a temperature ranging from 30° C. to the boiling point of the reaction mixture, preferably from 10 to 25° C. Chlorine, phosphorous trichloride, phosphorous pentachloride and sulforyl chloride can be used as halogenating agents to introduce chlorine atoms (X=Cl); bromine to introduce bromine atoms (X=Br); iodine to introduce iodine atoms (X=I).

Preferred solvents for carrying out the halogenation reaction are chlorinated hydrocarbons (methylene chloride, chloroform, carbon tetrachloride), aromatic hydrocarbons (benzene, toluene, xylene, chlorobenzene, etc.), ethers (diethyl ether, diisopropyl ether, dimethoxyethane, dioxane, tetrahydrofuran, etc.), esters (ethyl acetate, etc.), nitriles (acetonitrile, benzonitrile, etc.).

The reaction between the compounds having general formulae (V) and (VI) (scheme B) is preferably carried out in the presence of one or more inert organic solvents and in the presence of an inorganic or organic base, at a temperature ranging from −10° C. to the boiling point of the reaction mixture.

Organic solvents which can be used for the purpose are for example aromatic hydrocarbons (benzene, toluene, xylene, chlorobenzene, etc.), ethers (diethyl ether, diisopropyl ether, dimethoxyethane, dioxane, tetrahydrofuran, etc.), esters (ethyl acetate, etc.), alcohols and glycols (methanol, ethanol, methylcellosolve, ethylene glycol, etc.), ketones (acetone, methylethylketone, methylpropylketone, methylisobutylketone, etc.), nitrites (acetonitrile, benzonitrile, etc.), aprotic dipolar solvents (dimethylformamide, dimethylacetamide, hexamethylphosphorotriamide, dimethyl-sulfoxide, sulfolane, N-methyl-pyrrolidone, etc.).

Inorganic bases which can be used for the purpose are, for example, sodium or potassium hydrides, hydroxides and carbonates.

Organic bases which can be used for the purpose are, for example, triethylamine, pyridine, 4-dimethylaminopyridine, diazabicyclo-octane (DABCO), diazabicycloundecene (DBU).

The reaction can also be advantageously carried out in a biphasic system using, as solvents, water and an organic solvent immiscible therewith, in the presence of phase transfer catalysts, according to the procedure described by Dehmlow and Dehmlow in "Phase Transfer Catalysis" (1983), Verlag Chemie.

The intermediates having general formulae (II), (III), (V) and (VI), when not known in themselves, can be prepared with methods known in organic chemical practice. In particular, the phenylpyrazolones having general formula (II) can be obtained starting from the corresponding benzoylacetates substituted by means of reaction with a hydrazine having the formula $R_1NHNH_2$, analogously to the procedure described, for example, in "The chemistry of heterocyclic compounds", Vol. 20, (1964), A. Weissberger Ed., John Wiley & Sons.

As already mentioned, the compounds having general formula (I) have a high herbicidal activity which makes them suitable for use in the agrarian field to defend useful crops from weeds.

In particular, the compounds, object of the present invention, are effective in controlling numerous monocotyledon and dicotyledon weeds, both in pre-emergence and post-emergence.

At the same time, these compounds show compatibility or absence of toxic effects with respect to useful crops in pre-emergence and post-emergence treatment.

Examples of weeds which can be effectively controlled sing the compounds having general formula (I) are:, *Abutilon theofrasti, Alisma plantago,* Amaranthus spp., *Amni maius, Capsella bursa pastoris, Chenopodium album, Convolvulus septum, Galium aparine, Geranium dissectum,* Ipomea spp., Matricaria spp., *Papaver rhoaes, Phaseolus aureus, Polygonum persicaria, Portulaca oleracea, Sida spinosa, Sinapsis arvensis, Solanum nigrum, Stellaria media,* Veronica spp., Viola spp., Xanthium spp., *Alopecurus myosuroides, Avena fatua,* Cyperus spp., *Digitaria sanguinalis,* Echinocloa spp., *Heleocaris avicularis,* Heteranthera spp., Panicum spp., Poa spp., Scirpus spp., Sorghum spp., etc.

At the doses used for agrarian applications, the above compounds do not have any toxic effects with respect to important crops such as rice (*Oryza sativa*), wheat (Triticum spp.), barley (*Hordeum vulgare*), maize (*Zea mais*), soybean (*Glicine max*), etc.

A further object of the present invention relates to a method for controlling weeds in cultivated areas by the application of the compounds having general formula (I).

The quantity of compound to be applied to obtain the desired effect can vary in relation to various factors such as, for example, the compound used, the crop to be preserved, the weed to be attacked, the degree of infestation, the climatic conditions, the characteristics of the soil, the application method, etc.

Doses of compound ranging from 1 to 1000 g per hectare generally provide sufficient control.

For practical use in agriculture, it is often advantageous to use compositions with a herbicidal activity containing, as active substance, one or more of the compounds having general formula (I), optionally also as a mixture of isomers.

Compositions can be used in the form of dry powders, wettable powders, emulsifiable concentrates, microemulsions, pastes, granulates, solutions, suspensions, etc.: the selection of the type of composition will depend on the specific use.

The compositions are prepared according to known methods, o for example by diluting or dissolving the active substance with a solvent medium and/or solid diluent, optionally in the presence of surface-active agents.

Solid inert diluents, or carriers, which can be used are kaolin, alumina, silica, talc, bentonite, chalk, quartz, dolomite, attapulgite, montmorillonite, diatomaceous earth, cellulose, starch, etc.

Liquid inert diluents which can be used are water, or organic solvents such as aromatic hydrocarbons (xylols, mixtures of alkylbenzenes, etc.), aliphatic hydrocarbons (hexane, cyclohexane, etc.), halogenated aromatic hydrocarbons (chlorobenzene, etc.), alcohols (methanol, propanol, butanol, octanol, etc.), esters (isobutyl acetate, etc.), ketones (acetone, cyclohexanone, acetophenone, isophorone, ethylamylketone, etc.), or vegetable or mineral oils or their mixtures, etc.

Surface-active agents which can be used are wetting and emulsifying agents of the non-ionic type (polyethoxylated alkylphenols, polyethoxylated fatty alcohols, etc.), anionic type (alkylbenzenesulfonates, alkylsulfonates, etc.), cationic type (alkylammonium quaternary salts etc.).

Dispersing agents (for example lignin and its salts, derivatives of cellulose, alginates, etc.), stabilizers (for example antioxidants, U.V. absorbers, etc.) can also be added.

To widen the range of action of the above compositions, it is possible to add other active ingredients such as, for example, other herbicides, fungicides, insecticides or acaricides, fertilizers, etc.

Examples of other herbicides which can be added to the compositions containing one or more compounds having general formula (I) are the following:
acetochlor, acifluorfen, aclonifen, AKH-7088, alachlor, alloxydim, ametryn, amidosulfuron, amitrole, anilofos, asulam, atrazine, azafenidin (DPX-R6447), azimsulfuron (DPX-A8947), aziprotryne, benazolin, benfluralin, benfuresate, bensulfuron, bensulide, bentazone, benzofenap, benzthiazuron, bifenox, bilanafos, bispyribac-sodium (KIH-2023), bromacil, bromobutide, bromofenoxim, bromoxynil, butachlor, butamifos, butenachlor, butralin, butroxydim, butylate, cafenstrole (CH-900), carbetamide, carfentrazone-ethyl (F8426), chlomethoxyfen, chloramben, chlorbromuron, chlorbufam, chlorflurenol, chloridazon, chlorimuron, chlornitrofen, chlorotoluron, chloroxuron, chlorpropham, chlorsulfuron, chlorthal, chlorthiamid, cinidon ethyl, cinmethylin, cinosulfuron, clethodim, clodinafop, clomazone, clomeprop, clopyralid, cloransulam-methyl (XDE-565), cumyluron (JC-940), cyanazine, cycloate, cyclosulfamuron (AC-322140), cycloxydim, cyhalofop-butyl (XDE-537), 2,4-D, 2,4-DB, daimuron, dalapon, desmedipham, desmetryn, dicamba, dichlobenil, dichlorprop, dichlorprop-P, diclofop, diclosulam (XDE-564), diethatyl, difenoxuron, difenzoquat, diflufenican, diflufenzopyr (SAN 835H), dimefuron, dimepiperate, dimethachlor, dimethametryn, dimethenamid, dinitramine, dinoseb, dinoseb acetate, dinoterb, diphenamid, dipropetryn, diquat, dithiopyr, 1-diuron, eglinazine, endothal, epoprodan (MK-243), EPTC, esprocarb, ethalfluralin, ethametsulfuron-methyl (DPX-A7881), ethidimuron, ethiozin (SMY 1500), ethofumesate, ethoxyfen-ethyl (HC-252), ethoxysulfuron (HOE 095404), etobenzanid (HW 52), fenoxaprop, fenoxaprop-P, fentrazamide (BAY YRC 2388), fenuron, flamprop, flamprop-M, flazasulfuron, fluazifop, fluazifop-P, fluchloralin, flumetsulam (DE-498), flumiclorac-pentyl, flumioxazin, flumipropin, fluometuron, fluoroglycofen, fluoronitrofen, flupoxam, flupropanate, flupyrsulfuron (DPX-KE459), flurenol, fluridone, flurochloridone, fluroxypyr, flurtamone, fluthiacet-methyl (KIH-9201), fluthiamide (BAY FOE 5043), fomesafen, fosamine, furyloxyfen, glufosinate, glyphosate, halosulfuron-methyl (NC-319), haloxyfop, haloxyfop-P-methyl, hexazinone, imazamethabenz, mazamox (AC-299263), imazapic (AC-263222), imazapyr, imazaquin, imazethapyr, imazosulfuron, ioxynil, isopropalin, isopropazol (JV 485), isoproturon, isouron, isoxaben, isoxaflutole (RPA 201772), isoxapyrifop, KPP-421, lactofen, lenacil, linuron, LS830556, MCPA, MCPA-thioethyl, MCPB, mecoprop, mecoprop-P, mefenacet, metamitron, metazachlor, methabenzthiazuron, methazole, methoprotryne, methyldymron, metobenzuron, metobromuron, metolachlor, metosulam (DE-511), metoxuron, metribuzin, metsulfuron, molinate, monalide, monolinuron, naproanilide, napropamide, naptalam, NC-330, neburon, nicosulfuron, nipyraclofen, norflurazon, orbencarb, oryzalin, oxadiargyl, oxadiazon, oxasulfuron (CGA-277476), oxaziclomefone (MY-100), oxyfluorfen, paraquat, pebulate, pendimethalin, pentanochlor, pentoxazone (KPP-314), phenmedipham, picloram, piperophos, pretilachlor, primisulfuron, prodiamine, proglinazine, prometon, prometryne, propachlor, propanil, propaquizafop, propazine, propham, propisochlor, propyzamide, prosulfocarb, prosulfuron (CGA-152005), pyraflufenethyl (ET-751), pyrazolynate, pyrazosulfuron, pyrazoxyfen, pyribenzoxim (LGC-40863), pyributicarb, pyridate, pyriminobac-methyl (KIH-6127), pyrithiobac-sodium (KIH-2031), quinclorac, quinmerac, quizalofop, quizalofop-P, rimsulfuron, sethoxydim, siduron, simazine, simetryn, sulcotrione, sulfentrazone (F6285), sulfometuron (DPX-5648), sulfosulfuron (MON 37500), 2,3,6-TBA, TCA-sodium, tebutam, tebuthiuron, tepraloxydim (BAS 620H), terbacil, terbumeton, terbuthylazine, terbutryn, thenylchlor (NSK-850), thiazafluron, thiazopyr (MON 13200), thidiazimin, thifensulfuron, thiobencarb, tiocarbazil, tioclorim, tralkoxydim, tri-allate, triasulfuron (CGA-131036), triaziflam (IDH-1105), tribenuron, triclopyr, trietazine, trifluralin, triflusulfuron-methyl (DPX-66037), UBI-C4874, vernolate.

The concentration of active substance in the above compositions can vary within a wide range, depending on the active compound, applications for which they are destined, environmental conditions and type of formulation adopted.

The concentration of active substance generally ranges from 1 to 90%, preferably from 5 to 50%.

The following examples are provided for illustrative purposes but do not limit the scope of the present invention.

EXAMPLE 1

27) Synthesis of 4-chloro-3-[4-chloro-2-fluoro-5-(5-trifluoromethyl-1,3,4-thiadiazol-2-yloxy)phenyl]-5-difluoromethoxy-1-methylpyrazole (Compound Nr. 1).

9.6 g (28.3 mmoles) of tetrabutylphosphonium bromide are added to a solution of 30 g (76 mmoles) of 3-[4-chloro-2-fluoro-5-(5-trifluoromethyl-1,3,4-thiadiazol-2-yloxy) phenyl]-5-hydroxy-1-methylpyrazole in 350 ml of dichloromethane. The reaction environment is saturated with chlorodifluoromethane and 1700 ml of sodium hydroxide at 50% are added dropwise, the reaction mixture being maintained at room temperature and under vigorous stirring. At the end of the addition, the mixture is maintained under stirring for a further two hours. It is poured into water and ice; the phases are separated and the aqueous phase is extracted with dichloromethane (3×400). The joined organic phases are washed first with a solution of ammonium chloride, then with brine until neutral pH and are subsequently anhydrified with sodium sulfate and concentrated under vacuum. The raw product is purified by means of silica gel chromatography using a mixture of hexane/ethyl acetate: 7.5/2.5 as eluant. 18.6 g of a product corresponding to 3-[4-chloro-2-fluoro-5-(5-trifluoromethyl-1,3,4-thiadiazol-2-yloxy)phenyl]-5-difluoromethoxy-1-methylpyrazole are obtained (yield 55%).

0.92 ml (11.36 mmoles) of sulfuryl chloride are added dropwise to 5 g (11.25 mmoles) of the product thus obtained, dissolved in 50 ml of acetonitrile, the mixture being maintained under stirring at room temperature. After two hours of reaction, the mixture is carefully poured into 200 ml of a saturated solution of sodium bicarbonate and the resulting mixture is extracted with ethyl acetate (3×100). The joined organic phases are washed with a saturated solution of sodium chloride, anhydrified with sodium sulfate and concentrated under vacuum. 5.28 g of 4-chloro-3-[4-chloro-2-fluoro-5-(5-tri-fluoromethyl-1,3,4-thiadiazol-2-yloxy) phenyl]-5-difluoromethoxy-1-methylpyrazole are obtained (yield 98%), as a white solid having a melting point at 82–84° C.

$^1$H-NMR (CDCl$_3$) δ at 3.82 (3H, s); 6.70 (1H, t, J=72.2 Hz); 7.37 (1H, d, J=9.0 Hz); 7.68 (1H, d, J=6.2 Hz).

$^{19}$F-NMR (CDCl$_3$): δ at −111.10 (1F, bs); −81.49 (2F, d, J=72.3 Hz); −60.40 (3F, s)

EXAMPLE 2

Synthesis of ethyl 2-[2-chloro-5-(4-chloro-5-difluoromethoxy-1-methylpyrazol-3-yl)-4-fluoro-phenoxymethyl]-3-furancarboxylate (Compound Nr. 2).

2.32 g (16.81 mmoles) of potassium carbonate are added to a solution prepared with 5 g (15.28 mmoles) of 4-chloro-3-(4-chloro-2-fluoro-5-hydroxyphenyl)-5-difluoromethoxy-1-methylpyrazole, 3.92 g (16.81 mmoles) of ethyl 2-bromomethyl-3-furancarboxylate and 100 ml of acetone. The mixture is heated to reflux temperature under stirring for 2 hours. The raw product is then poured into 500 ml of a saturated solution of sodium chloride and extracted with ethyl acetate (3×150). The joined organic phases are washed with a saturated solution of sodium chloride, anhydrified with sodium sulfate and concentrated under vacuum. The raw product is purified by means of silica gel chromatography using a mixture of hexane/ethyl acetate: 8/2 as eluant. 7.18 g of ethyl 2-[2-chloro-5-(4-chloro-5-difluoromethoxy-1-methylpyrazol-3-yl)-4-fluorophenoxymethyl]-3-furancarboxylate (Compound Nr. 2) are obtained (yield 98%), as a white solid having a melting point of 59–61° C.
δH (CDCl$_3$): 1.29 (3H, t, J=7.17 Hz); 3.82 (3H, s); 4.27 (2H, q; J 7.17 Hz); 5.43 (2H, s); 6.70 (1H, t, J=72.4 Hz); 6.73 (1H, d, J=1.9 Hz); 7.20–7.26 (2H, m); 7.42 (1H, d, J=1.9).
δ$^{19}$F: −120.3 (1H, bs); −81.45 (2H, d, J=72.4 Hz).

EXAMPLE 3

Preparation of Compounds Nr. 3–26.

Operating analogously to the procedure described in Example 1 or Example 2, the following compounds were prepared:

4-chloro-3-[4-chloro-2-fluoro-5-(5-methyl-1,3,4-thiadiazol-2-yloxy)phenyl]-5-difluoromethoxy-1-methylpyrazole (compound Nr. 3);

4-chloro-3-[4-chloro-2-fluoro-5-(5-ethylthio-1,3,4-thiadiazol-2-yloxy)phenyl]-5-difluoromethoxy-1-methylpyrazole (compound Nr. 4);

4-chloro-3-[4-chloro-2-fluoro-5-(5-ethylsulfonyl-1,3,-4-thiadiazol-2-yloxy)phenyl]-5-difluoromethoxy-1-methylpyrazole (compound Nr. 5);

4-chloro-3-{4-chloro-2-fluoro-5-[5-(1,1,2,2-tetrafluoroethylthio)-1,3,4-thiadiazol-2-yloxy]phenyl}-5-difluoromethoxy-1-methylpyrazole (compound Nr. 6);

4-chloro-3-[4-chloro-2-fluoro-5-(5-trifluoromethyl-1,3,4-thiadiazol-2-yloxy)phenyl]-5-(1,1,2,2-tetrafluoroethoxy)-1-methylpyrazole (compound Nr. 7);

ethyl 2-{2-chloro-5-[4-chloro-5-(1,1,2,2-tetrafluoroethoxy)-1-methylpyrazol-3-yl]-4-fluorophenoxymethyl}-3-furancarboxylate (compound Nr. 8);

methyl 3-[2-chloro-5-(4-chloro-5-difluoromethoxy-1-methylpyrazol-3-yl)-4-fluoro-phenoxymethyl]-2-thiophenecarboxylate (compound Nr. 9);

4-chloro-3-[4-chloro-2-fluoro-5-(5-formylthiophen-2-yloxy)phenyl]-5-difluoromethoxy-1-methylpyrazole (compound Nr. 10);

4-chloro-3-[4-chloro-2-fluoro-5-(5-methoxyiminomethylthiophen-2-yloxy)phenyl]-5-difluoromethoxy-1-methylpyrazole (compound Nr. 11);

4-chloro-3-[4-chloro-2-fluoro-5-(4-formyl-2-methylthiazol-5-yloxy)phenyl]-5-difluoromethoxy-1-methylpyrazole (compound Nr. 12);

4-chloro-3-[4-chloro-2-fluoro-5-(4-methoxyiminomethyl-2-methylthiazol-5-yloxy)phenyl]-5-difluoromethoxy-1-methyl-pyrazole (compound Nr. 13);

4-chloro-3-[4-chloro-2-fluoro-5-(2-methylthiazol-4-yl)methoxyphenyl]-5-difluoromethoxy-1-methylpyrazole (compound Nr. 14);

4-chloro-3-[4-chloro-2-fluoro-5-(5-bromo-2-methylthiazol-4-yl)methoxyphenyl]-5-difluoromethoxy-1-methylpyrazole (compound Nr. 15);

4-chloro-3-[4-chloro-2-fluoro-5-(4-formyl-1,3-dimethylpyrazol-5-yloxy)phenyl]-5-difluoromethoxy-1-methylpyrazole (compound Nr. 16);

4-chloro-3-[4-chloro-5-(1,3-dimethyl-4-methoxyiminomethylpyrazol-5-yloxy)-2-fluorophenyl]-5-difluoromethoxy-1-methylpyrazole (compound Nr. 17);

ethyl 5-[2-chloro-5-(4-chloro-5-difluoromethoxy-1-methylpyrazol-3-yl)-4-fluorophenoxymethyl]-3-isoxazole-carboxylate (compound Nr. 18);

ethyl 5-[2-chloro-5-(4-chloro-5-difluoromethoxy-1-methylpyrazol-3-yl)-4-fluorophenoxymethyl]-3-furoate (compound Nr. 19);

ethyl 2-[2-chloro-5-(4-chloro-5-difluoromethoxy-1-methylpyrazol-3-yl)-4-fluorophenoxymethyl-4-thiazole-carboxylate (compound Nr. 20);

4-chloro-3-[4-chloro-5-(5-ethyl-1,3,4-thiadiazol-2-yloxy)-2-flurophenyl]-5-difluoromethoxy-1-methylpyrazole (compound Nr. 21);

4-chloro-3-[4-chloro-2-fluoro-5-(5-isopropyl-1,3,4-thiadiazol-2-yloxy)phenyl]-5-difluoromethoxy-1-methylpyrazole (compound Nr. 22);

4-chloro-3-[4-chloro-2-fluoro-5-(5-methoxymethyl-1,3,4-thiadiazol-2-yloxy)phenyl]-5-difluoromethoxy-1-methylpyrazole (compound Nr. 23);

4-chloro-3-{4-chloro-2-fluoro-5-[5-(3-trifluoromethylphenyl)-1,3,4-thiadiazol-2-yloxy]phenyl}-5-difluoromethoxy-1-methylpyrazole (compound Nr. 24);

4-chloro-3-[4-chloro-2-fluoro-5-(1-methyl-2-trifluoromethyl-1,3,4-thiadiazol-5-yloxy)phenyl]-5-difluoromethoxy-1-methylpyrazole (compound Nr. 25);

4-chloro-3-[4-chloro-2-fluoro-5-(3-nitrothien-2-yloxy)phenyl]-5-difluoromethoxy-1-methylpyrazole (compound Nr. 26);

EXAMPLE 4

Determination of the Herbicidal Activity and Phytotoxicity in Post-Emergence.

The herbicidal activity of the compounds of the invention in post-emergence was evaluated according to the following operating procedure.

The vegetable species of interest (weeds or crops) were planted in vases having a diameter of over 10 cm, a height of 10 cm and containing sandy soil. 10 vases were used for each vegetable species.

Water was added to each vase in a suitable quantity for a good germination of the seeds. The vases were then divided into two groups, each group containing 5 vases for each weed or crop.

Fifteen days after sowing (ten in the case of wheat), i.e. when the small weed plants and crops, depending on the species, were 10–15 cm high, the first group of vases was treated with a hydro-acetone dispersion containing acetone at 10% by volume, the product to be evaluated at the desired concentration and Tween 20 at 0.5%.

The second group was only treated with a hydro-acetone solution containing acetone at 10% by volume and Tween 20 at 0.5%, and was used as a comparison (blank).

All the vases were kept under observation in a conditioned environment under the following environmental conditions:

temperature: 24° C.
relative humidity: 60%
photoperiod: 16 hours
light intensity: 10,000 lux Every two days, the vases were uniformly watered to ensure a sufficient degree of humidity for a good development of the plants.

15 days after treatment, the herbicidal activity was evaluated on the basis of the following scale of values referring to the percentage of damage measured on the treated plants with respect to those not treated (blank):

0=0–10% of damage
1=11–30%
2=31–50%
3=51–70%
4=71–90%
5=91% damage—death of the plant Table 1 indicates the results obtained treating the vegetable species listed below with compounds 1 and 2 at a dose of 50 g/ha:

*Abutilon theofrasti* (AT); *Amarantus retroflexus* (AR); *Chenopodium album* (CA); *Convolvulus sepium* (CS); *Galium aparine* (GA); *Ipomea purpurea;* (IP) *Portulaca oleracea* (PO); *Solanum nigrum* (SN); *Stellaria media* (SM); maize (M).

TABLE 1

Herbicidal activity in post-emergence at a dose of 50 g/ha

| | Vegetable Species | | | | | | | | | |
|---|---|---|---|---|---|---|---|---|---|---|
| | AT | AR | CA | CS | GA | IP | PO | SN | SM | M |
| Compound Nr. 1 | 5 | 5 | 5 | 5 | 5 | 5 | 5 | 5 | 5 | 0 |
| Compound Nr. 2 | 5 | 5 | 5 | 5 | 4 | 5 | 5 | 5 | 5 | 1 |
| Compound Nr. 3 | 5 | 5 | 5 | 5 | 5 | 5 | 5 | 5 | 5 | 2 |
| Compound Nr. 10 | 5 | 5 | 5 | 5 | 4 | 5 | 5 | 5 | n.d. | 1 |
| Compound Nr. 12 | 5 | 5 | 5 | 5 | 4 | 5 | 4 | 5 | n.d. | 1 |
| Compound Nr. 18 | 5 | 5 | 5 | 5 | 5 | 5 | 5 | 6 | 5 | 1 |
| Compound Nr. 20 | 5 | 5 | 5 | 5 | 5 | 5 | 5 | 5 | 5 | 0 |

What is claimed is:

1. Phenylpyrazoles having general formula (I):

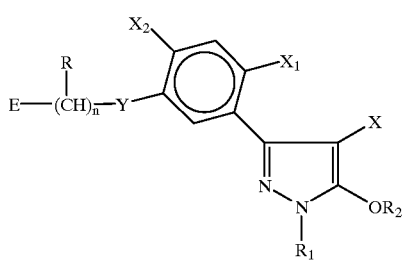

wherein:
$R_1$ and $R_2$, the same or different, represent a $C_1$–$C_4$ alkyl or haloalkyl group;
X represents a halogen atom;
$X_1$ represents a hydrogen atom, a chlorine atom or a fluorine atom;
$X_2$ represents a chlorine atom, a bromine atom, a $C_1$–$C_4$ haloalkyl group, a $C_1$–$C_4$ haloalkoxyl group;
Y represents an oxygen atom or a sulfur atom;
R represents a hydrogen atom or a $C_1$–$C_4$ alkyl group;
n represents 0 or 1;
E represents one of the following heterocyclic groups: 2-furanyl, 3-furanyl, 2-thiophenyl, 3-thiophenyl, 2-pyrrolyl, 3-pyrrolyl, 2-imidazolyl, 4-imidazolyl, 5-imidazolyl, 3-pyrazolyl, 4-pyrazolyl, 5-pyrazolyl, 1,2,4-triazol-3-yl, 1,2,4-triazol-5-yl, 1,2,4-triazol-3-on-5-yl, 1,2,3-triazol-4-yl, 1,2,3-triazol-5-yl, 5-tetrazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-oxadiazol-2-yl, 1,3,4-oxadiazol-2-on-5-yl, 1,3,4-thiadiazol-2-yl, 1,3,4-thiadiazol-2-on-5-yl, 1,2,4-oxadiazol-3-yl, 1,2,4-oxadiazol-5-yl, 1,2,4-thiadiazol-3-yl, 1,2,4-thiadiazol-5-yl; said groups can be substituted by one or more groups—the same or different—selected from a halogen atom, a $C_1$–$C_6$ alkyl or haloalkyl group, a $C_1$–$C_6$ alkoxyl or haloalkoxyl group, a $C_2$–$C_6$ alkoxyalkyl or haloalkoxyalkyl group, a $C_1$–$C_6$ alkylthio or haloalkylthio group, a $C_1$–$C_6$ alkylsulfinic or haloalkylsulfinic group, a $C_1$–$C_6$ alkylsulfonic or haloalkylsulfonic group, an alkoxycarbonyl or haloalkoxycarbonyl group, an aminocarbonyl group optionally substituted by one or two $C_1$–$C_4$ alkyl groups or by a $C_2$–$C_5$ alkylene chain, a cyano group, a formyl group, an alkylcarbonyl or haloalkylcarbonyl group, an alkoxyiminoalkyl or haloalkoxyiminoalkyl group, a phenyl group optionally substituted, in turn, by halogen atoms, $C_1$–$C_4$ alkyl or haloalkyl groups, $C_1$–$C_4$ alkoxyl or haloalkoxyl groups.

2. The phenylpyrazoles according to claim 1 selected from the group consisting of:

1) 4-chloro-3-[4-chloro-2-fluoro-5-(5-trifluoromethyl-1,3,4-thiadiazol-2-yloxy)phenyl]-5-difluoromethoxy-1-methylpyrazole;

2) ethyl 2-[2-chloro-5-(4-chloro-5-difluoromethoxy-1-methylpyrazol-3-yl)-4-fluoro-phenoxymethyl]-3-furancarboxylate;

3) 4-chloro-3-[4-chloro-2-fluoro-5-(5-methyl-1,3,4-thiadiazol-2-yloxy)phenyl]-5-difluoromethoxy-1-methylpyrazole;

4) 4-chloro-3-[4-chloro-2-fluoro-5-(5-ethylthio-1,3,4-thiadiazol-2-yloxy)phenyl]-5-difluoromethoxy-1-methylpyrazole;

5) 4-chloro-3-[4-chloro-2-fluoro-5-(5-ethylsulfonyl-1,3,-4-thiadiazol-2-yloxy)phenyl]-5-difluoromethoxy-1-methylpyrazole;

6) 4-chloro-3-{4-chloro-2-fluoro-5-[5-(1,1,2,2-tetrafluoroethylthio)-1,3,4-thiadiazol-2-yloxy]phenyl}-5-difluoromethoxy-1-methylpyrazole;

7) 4-chloro-3-[4-chloro-2-fluoro-5-(5-trifluoromethyl-1,3,4-thiadiazol-2-yloxy)phenyl]-5-(1,1,2,2-tetrafluoroethoxy)-1-methylpyrazole;

8) ethyl 2-{2-chloro-5-[4-chloro-5-(1,1,2,2-tetrafluoroethoxy)-1-methylpyrazol-3-yl]-4-fluorophenoxymethyl}-3-furancarboxylate;

9) methyl 3-[2-chloro-5-(4-chloro-5-difluorometh-oxy-1-methylpyrazol-3-yl)-4-fluoro-phenoxymethyl]-2-thiophenecarboxylate;

10) 4-chloro-3-[4-chloro-2-fluoro-5-(5-formylthiophen-2-yloxy)phenyl]-5-difluoromethoxy-1-methylpyrazole;

11) 4-chloro-3-[4-chloro-2-fluoro-5-(5-methoxyiminomethyl-thiophen-2-yloxy)phenyl]-5-difluoromethoxy-1-methyl-pyrazole;

12) 4-chloro-3-[4-chloro-2-fluoro-5-(4-formyl-2-methyl-thiazol-5-yloxy)phenyl]-5-difluoromethoxy-1-methylpyrazole;

13) 4-chloro-3-[4-chloro-2-fluoro-5-(4-ethoxyiminomethyl-2-methylthiazol-5-yloxy)phenyl]-5-difluoromethoxy-1-methyl-pyrazole;

14) 4-chloro-3-[4-chloro-2-fluoro-5-(2-methylthiazol-4-yl)methoxyphenyl]-5-difluoromethoxy-1-methylpyrazole;

15) 4-chloro-3-[4-chloro-2-fluoro-5-(5-bromo-2-methylthi-azol-4-yl)methoxyphenyl]-5-difluoromethoxy-1-methyl-pyrazole;

16) 4-chloro-3-[4-chloro-2-fluoro-5-(4-formyl-1,3-dimeth-ylpyrazol-5-yloxy)phenyl]-5-difluoromethoxy-1-methyl-pyrazole.

17) 4-chloro-3-[4-chloro-5-(1,3-dimethyl-4-methoxyimino-methylpyrazol-5-yloxy)-2-fluorophenyl]-5-difluoromethoxy- 1-methylpyrazole
18) ethyl 5-[2-chloro-5-(4-chloro-5-difluoromethoxy-1-methylpyrazol-3-yl)-4-fluorophenoxymethyl-3-isoxazole-carboxylate;
19) ethyl 5-[2-chloro-5-(4-chloro-5-difluoromethoxy-1-methylpyrazol-3-yl)-4-fluorophenoxymethyl-3-furoate;
20) ethyl 2-[2-chloro-5-(4-chloro-5-difluoromethoxy-1-methylpyrazol-3-yl)-4-fluorophenoxymethyl-4-thiazole-carboxylate;
21) 4-chloro-3-[4-chloro-5-(5-ethyl-1,3,4-thiadiazol-2-yl-oxy)-2-flurophenyl]-5-difluoromethoxy-1-methylpyrazole;
22) 4-chloro-3-[4-chloro-2-fluoro-5-(5-isopropyl-1,3,4-thiadiazol-2-yloxy)phenyl]-5-difluoromethoxy-1-methylpyrazole;
23) 4-chloro-3-[4-chloro-2-fluoro-5-(5-methoxymethyl-1,3,4-thiadiazol-2-yloxy)phenyl]-5-difluoromethoxy-1-methylpyrazole;
24) 4-chloro-3-{4-chloro-2-fluoro-5-[5-(3-trifluoromethyl-phenyl)-1,3,4-thiadiazol-2-yloxy]phenyl}-5-difluoromethoxy-1-methylpyrazole;
25) 4-chloro-3-[4-chloro-2-fluoro-5-(1-methyl-2-trifluoromethyl-1,3,4-thiadiazol-5-yloxy)phenyl]-5-difluoromethoxy-1-methylpyrazole;
26) 4-chloro-3-[4-chloro-2-fluoro-5-(3-nitrothien-2 -yl-oxy)phenyl]-5-difluoromethoxy-1-methylpyrazole.

3. A process for the preparation of the compounds having general formula (I) wherein a phenyl-pyrazolone having general formula (II) is reacted with a compound having general formula (III) to give a phenylpyrazolyl ether having general formula (IV) which is subsequently converted to the end product having general formula (I) by treatment with a halogenating agent, according to the following general scheme A;

wherein E, R, $R_1$, $R_2$, X, $X_1$, $X_2$, Y and n have the meanings described above;

$L_1$ represents a halogen atom or an $OSO_2R_L$ group wherein $R_L$ represents a $C_1$–$C_4$ alkyl or haloalkyl group or a phenyl optionally substituted by $C_1$–$C_4$ alkyl or haloalkyl groups.

4. The process according to claim 3, wherein the reaction between the compound having general formula (II) and the compound having general formula (III) is carried out in the presence of one or more inert organic solvents and in the presence of an inorganic or organic base, at a temperature ranging from −10° C. to the boiling point of the reaction mixture and the treatment with a halogenation agent of the product having general formula (IV) is carried out in an inert organic solvent, at a temperature ranging from −30° C. to the boiling point of the reaction mixture.

5. A process for the preparation of the compounds having general formula (I) wherein a phenylpyrazole having general formula (V) is reacted with a compound having general formula (VI), according to the following general scheme B, in the presence of one or more inert organic solvents and in the presence of an inorganic or organic base, at a temperature ranging from −10° C. to the boiling point of the reaction mixture:

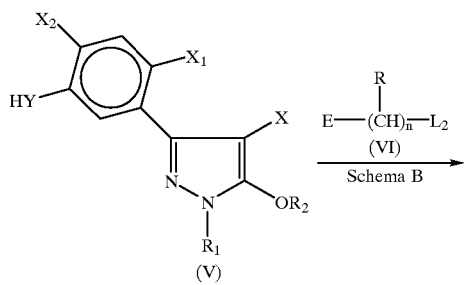

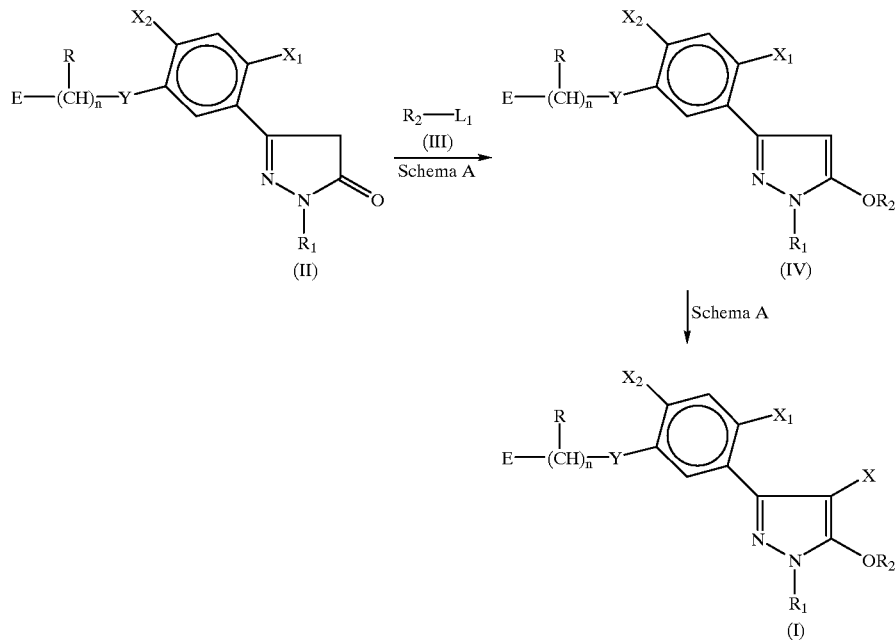

-continued

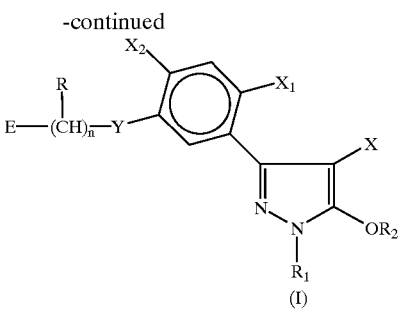

(I)

wherein E, R, $R_1$, $R_2$, X, $X_1$, $X_2$, Y and n have the meanings described above;

$L_2$ represents an $L_1$ group or, when n=0, it may also represent an $SO_2R_L$ group wherein $R_L$ has the meanings defined above.

6. Herbicidal compositions comprising solid carriers, liquid diluents, surface-active agents or other special additives and at least one of the compounds according to claim 1 or 2, at concentrations from 1 to 90%, also optionally as a mixture of isomers.

7. The compositions according to claim 6, also comprising other active ingredients such as herbicides, fungicides, insecticides, acaricides, fertilizers.

8. A method for controlling weeds in cultivated areas which consists in applying the herbicidal compositions according to claim 6, to said areas.

9. The method according to claim 8, wherein the active compounds are used at doses ranging from 1 to 1000 g per hectare.

* * * * *